United States Patent [19]
Danby et al.

[11] Patent Number: 5,754,085
[45] Date of Patent: *May 19, 1998

[54] FERROMAGNETIC YOKE MAGNETS FOR MEDICAL MAGNETIC RESONANCE STUDIES

[75] Inventors: Gordon T. Danby, Wading River; John W. Jackson, Shoreham, both of N.Y.; Hank Hsieh, Frascati, Italy

[73] Assignee: Fonar Corporation, Melville, N.Y.

[*] Notice: The terminal 29 months of this patent has been disclaimed.

[21] Appl. No.: 952,810

[22] Filed: Sep. 28, 1992

[51] Int. Cl.$^6$ .................................. G01V 3/00; H01F 7/00
[52] U.S. Cl. .................. 335/297; 335/216; 335/301; 335/306; 324/319
[58] Field of Search ...................... 335/216, 296–306; 324/318, 319, 320; 128/653.5

[56] References Cited

U.S. PATENT DOCUMENTS

| | | | |
|---|---|---|---|
| 4,641,119 | 2/1987 | Moore | 335/297 |
| 4,943,774 | 7/1990 | Breneman et al. | 324/318 |
| 4,985,678 | 1/1991 | Gangarosa et al. | 324/318 |
| 5,134,374 | 7/1992 | Breneman et al. | 324/319 |
| 5,194,810 | 3/1993 | Breneman et al. | 324/319 |

*Primary Examiner*—Cassandra C. Spyrou
*Assistant Examiner*—Raymond Barrera
*Attorney, Agent, or Firm*—Lerner, David, Littenberg, Krumholz & Mentlik

[57] ABSTRACT

A magnet for use in medical magnetic resonance studies and having a pair of ferromagnetic pole pieces supported by a ferromagnetic yoke which establishes a flux return path. Columns of the yoke are configured to maintain the magnetic field within the columns approximately constant in every cross section of the columns and to maximize access to the magnet gap.

19 Claims, 7 Drawing Sheets

FERROMAGNETIC YOKE MAGNETS FOR MEDICAL MAGNETIC RESONANCE STUDIES

CROSS-REFERENCE TO RELATED APPLICATION

The related U.S. patent application entitled Multiple Patient Scanning on a Magnetic Resonance Imaging Apparatus, of Raymond V. Damadian, filed concurrently herewith and commonly assigned, discloses methods of conducting magnetic resonance studies which can be carried out using the magnet structure disclosed and claimed herein.

BACKGROUND OF THE INVENTION

The present invention relates to magnets for medical magnetic resonance studies and more particularly to such magnets which comprise a ferromagnetic yoke as part of the magnet structure.

Medical magnetic resonance (MR) studies are typically carried out in strong magnetic fields greater than one kilogauss. In addition to a strong magnetic field, medical magnetic resonance studies typically require a magnetic field homogeneity of the order of a few parts per million. Considerable effort has been invested in improving magnets for medical MR with a goal toward achieving the field strengths required while attaining the necessary field homogeneity over a sufficiently large spatial volume in a structure that is clinically acceptable and commercially feasible.

One technique for improving magnet efficiency is to incorporate within the magnet structure a ferromagnetic yoke which not only comprises part of the structural support but which also defines a magnetic flux return path. The use of ferromagnetic return paths in medical magnetic resonance scanner magnets is disclosed in U.S. Pat. No. 4,675,609 to Danby et.al. Ferromagnetic yoke structure is likewise disclosed in U.S. Pat. No. 4,672,346 to Miyamoto et. al. In addition to improving efficiency, the incorporation of a ferromagnetic flux return path can also be used to eliminate strong leakage magnetic fields which are inherent in aircore solenoidal magnets.

It would be desirable to incorporate ferromagnetic yokes in medical MR magnets having a strong magnetic field, greater than 5 kilogauss. The stronger the magnetic field developed by the magnet, however, the more difficult it is to achieve a magnet structure which would be considered practical by the medical community for clinical use. To avoid magnetic saturation of the ferromagnetic yoke at high field strengths, the dimensions of the yoke cross sections along the flux return path become substantial. Greater yoke cross-sectional area results, of course, in an increase in magnet weight.

Additionally, larger yoke structure can result in obstructions which hinder easy access to and egress from the patient gap of the magnet where a patient is situated during magnetic resonance scanning. Any compromises to the required yoke design from the standpoint of flux return path reluctance, in order to accommodate patient access, can materially increase the magnetic leakage field and reduce the homogeneity of the magnetic field within the gap.

Accordingly, it is an object of the invention to provide a magnet having a ferromagnetic yoke with a strong field for use in medical magnetic resonance studies which has a large gap and a structure providing easy patient access.

It is another object of the invention to provide a magnet having a ferromagnetic yoke for medical magnetic resonance scanning and having a large patient gap and a large homogeneous field region within the patient gap.

It is another object of the invention to provide a magnet for medical magnetic resonance studies which has a ferromagnetic yoke with a structure that maximizes access to the patient gap of the magnet.

SUMMARY OF THE INVENTION

According to the invention a magnet for use in medical magnetic resonance studies develops a magnetic field within its gap. In a preferred embodiment, the field strength is in excess of five kilogauss. A pair of opposed ferromagnetic pole pieces face each other and define a patient-receiving gap between them for receiving the body of a patient to be studied by magnetic resonance. A ferromagnetic yoke supports the pole pieces in position facing each other.

The ferromagnetic yoke is comprised of upper and lower pole piece supports each for supporting a respective one of the pole pieces, and a plurality of ferromagnetic columns for supporting the upper pole piece support above the lower pole piece support. The upper and lower pole piece supports and the columns together establish a magnetic flux return path for magnetic flux which passes from one pole piece to the other through the patient gap.

Means for generating magnetic flux generates a magnetic flux flowing from one to the other of the pole pieces across the air gap and through the yoke back to the one of the pole pieces. Shimming means is provided for shimming the magnetic field within the gap between the pair of pole pieces to a uniformity sufficient to allow a medical magnetic resonance study to be performed on a patient while within the gap.

The yoke and pole pieces are symmetrical about an imaginary plane passing midway between the pole pieces and parallel to them, and each of the columns have a respective cross section which is minimum in a region midway between the pole pieces and which increases in directions toward the pole piece supports such that the magnetic field through every cross section along the length of a column is approximately equal.

In one preferred embodiment the yoke is comprised of four columns disposed uniformly around circular pole pieces, and the distance between adjacent columns is sufficient to allow the insertion of a patient between adjacent columns into the gap.

In another preferred embodiment the pole pieces are oval and the columns of the yoke are positioned at the corners of an imaginary rectangle. The space between any two adjacent columns is wide enough to allow convenient access to the patient gap of the magnet.

BRIEF DESCRIPTION OF THE DRAWING

Additional objects and features of the invention will appear from the following description of the preferred embodiments of the invention in conjunction with the accompanying drawing in which.

DETAILED DESCRIPTION OF THE PREFERRED EMBODIMENTS

Figure 1:
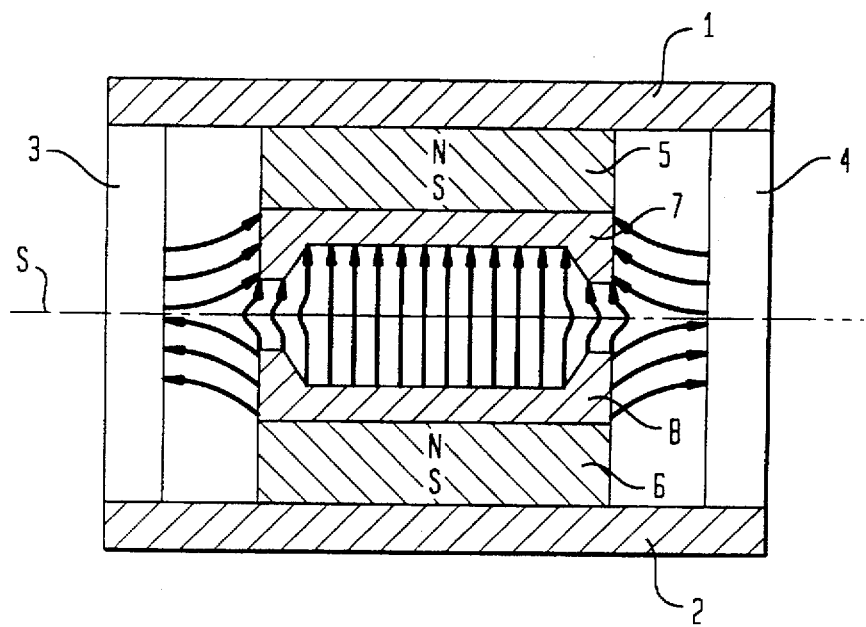
FIG. 1 is a vertical section of a conventional magnet used for magnetic resonance scanning.

In order to facilitate an appreciation of the improvements embodied in the claimed invention, a conventional magnet, illustrated in FIG. 1, will first be discussed. The prior art magnet has structure like that disclosed in U.S. Pat. No. 4,672,341 previously mentioned. This magnet is comprised of an upper plate 1 and a lower plate 2 supported by four columns. Two of the columns 3 and 4 are shown in the drawing. Permanent magnets 5 and 6 are supported by upper and lower plates 1 and 2, respectively, and pole pieces 7 and 8 respectively cover the magnets 5 and 6. The space between the pole pieces 7 and 8 is the patient-receiving gap of the magnet.

The permanent magnets 5 and 6 develop magnetic flux which crosses the gap between the pole pieces 7, 8 and which is depicted by arrows in the drawing. Arrows also depict leakage magnetic flux in the region of the gap which extends out to the columns 3 and 4. The magnet is symmetrical about an imaginary plane of symmetry S shown by a dashed line, which is midway between the pole pieces 7,8.

An inherent property of the symmetrical magnet structure is a symmetry in the magnetic field developed within the magnet. The leakage field, depicted by flux lines extending between the pole pieces 7,8 and the yoke columns 3,4 substantially does not cross the midplane S. For example, pole piece 8 corresponding to the North magnetic pole has a leakage field which extends from the pole piece 8 to the columns 3 and 4 in a region below the midplane S. On the other hand, leakage flux from the columns 3 and 4 extends to the pole piece 7, corresponding to the South magnetic pole, just in the region above the midplane S. On the midplane S the leakage field is substantially zero, and the only magnetic flux passing through the columns 3 and 4 through the midplane is due to the flux across the gap and returning to the other side of the gap through the flux return path comprised of the columns.

Figure 2:
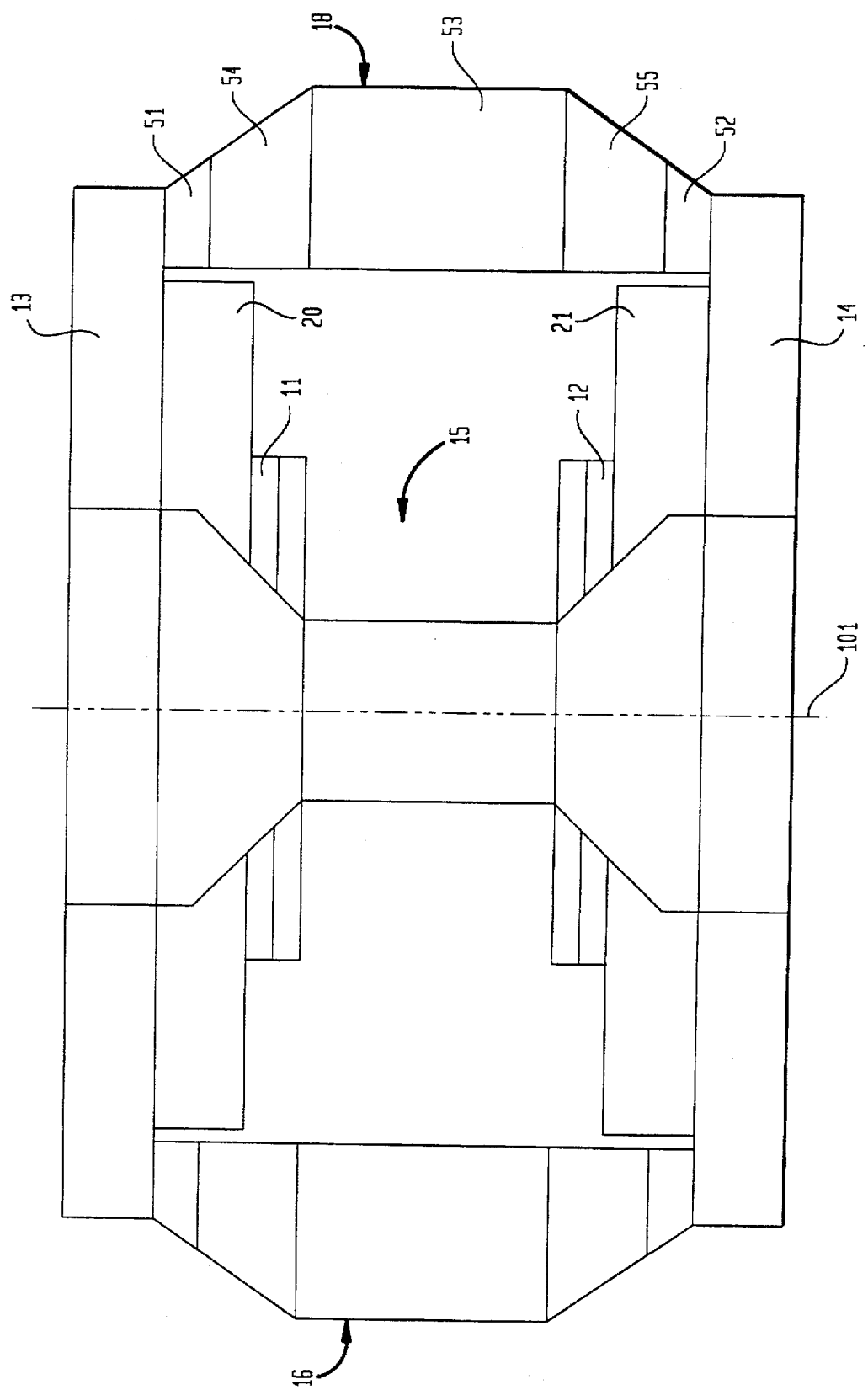
FIG. 2 is a front elevation of the magnet according to the invention.

The magnet according to the present invention, shown in FIG. 2, is comprised of a pair of ferromagnetic pole pieces 11 and 12 respectively mounted on an upper pole piece support 13 and a lower pole piece support 14. A patient-receiving gap 15 between the poles 11 and 12 is sufficiently large to receive the body of a patient who is to undergo study by magnetic resonance. Pole pieces 11 and 12 also define magnet central axis 101 extending through gap 15. The upper and lower pole piece supports 13, 14 are supported by a plurality of columns. The illustrated embodiment has four columns, 16-19, three of which are visible in the view shown. Conductive coils or windings 20 and 21 are energizable for developing a magnetic field which passes through the gap 15 between the pole pieces 11 and 12. A pair of annular ferromagnetic structures 22, 23 called shim bars are disposed on the pole faces of pole pieces 11, 12, respectively. The shim bars are used to reduce fringing of the magnetic field around the periphery of the pole pieces 11, 12, thereby increasing the volume of uniform magnetic field.

Figure 3:
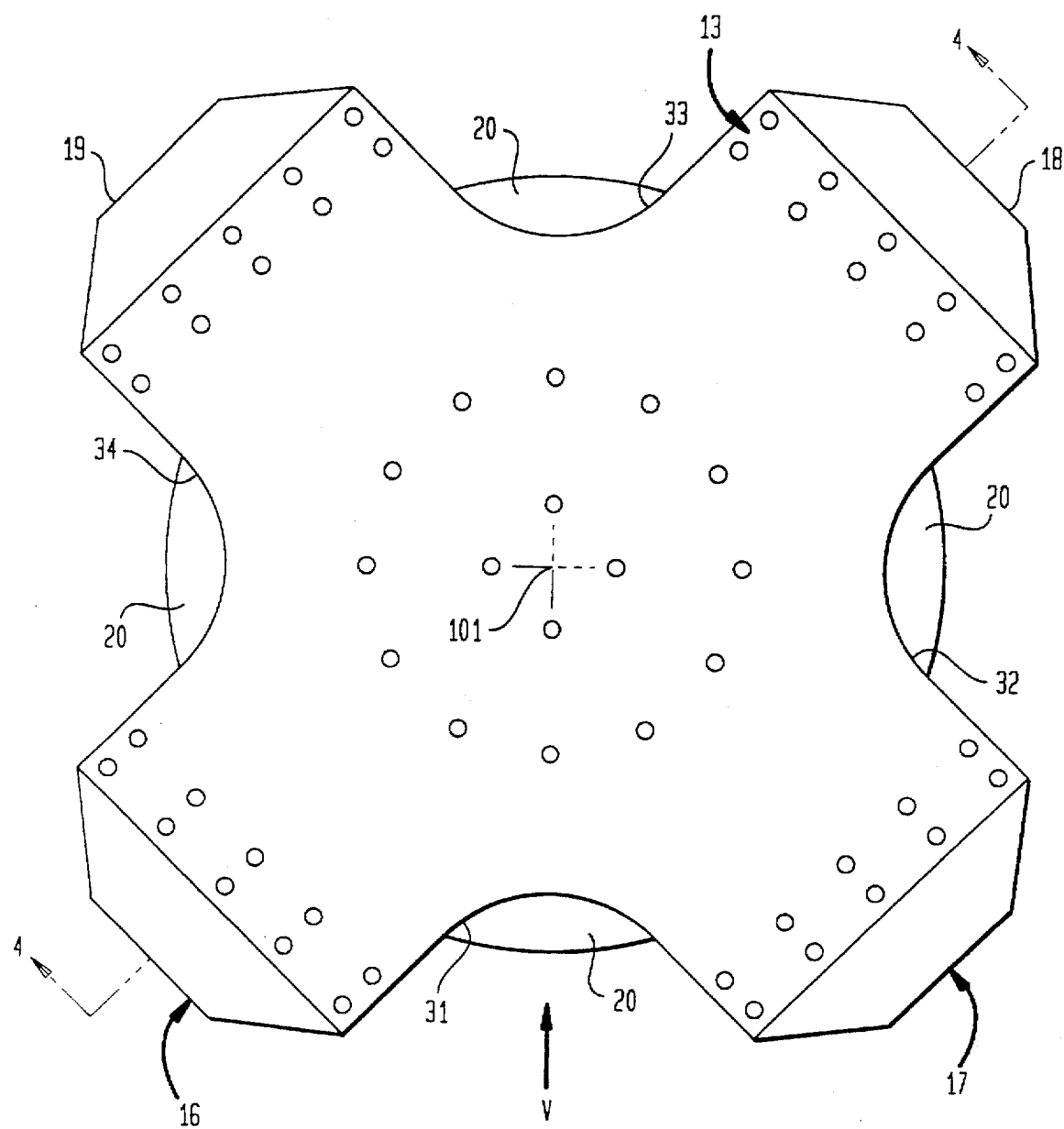
FIG. 3 is a plan view of the magnet according to the invention.

FIG. 3 is a plan view of the magnet according to the present invention. The pole piece support 13 has four legs 31-34 extending from a central region 35 of the support. The columns 16-19 together support the pole piece support 13, each at a respective one of the legs 31-34. The spaces between adjacent legs provide access to the patient gap of the magnet. For example, the space between the columns 16 and 17, viewed from direction by a V in FIG. 5, allows a patient to enter and exit the patient gap between the columns 16 and 17.

Figure 4:
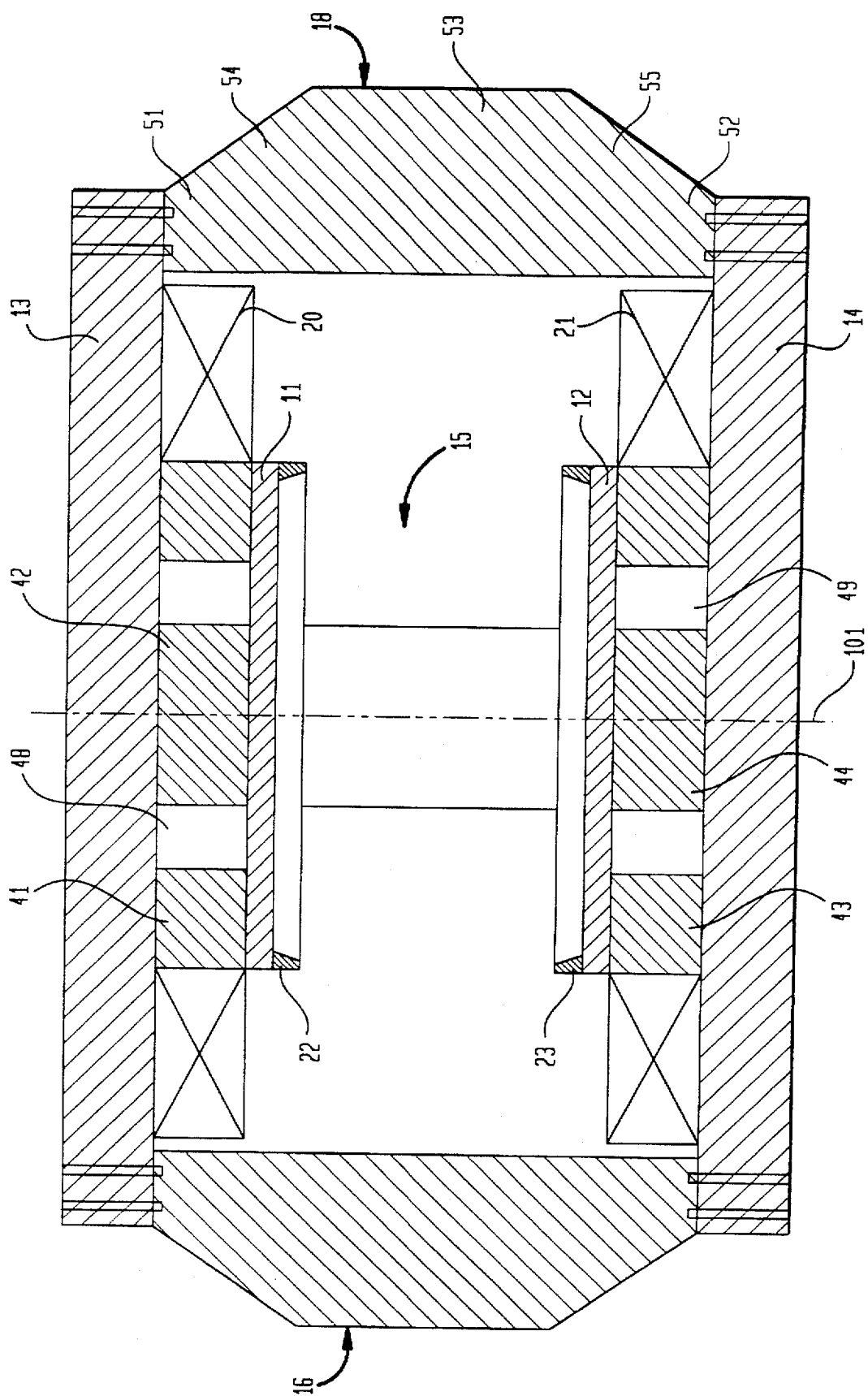
FIG. 4 is a vertical section of the magnet according to the invention taken along the section line 4—4 in FIG. 3.

FIG. 4 is a vertical section taken along the line 4—4 in FIG. 3. The upper and lower supports 13, 14 are secured to the columns, for example, by threaded shafts. The pole pieces 11 and 12 are secured to the pole piece supports 13 and 14 through the intermediary of pole stems. In the preferred embodiment shown, each pole stem is comprised of two elements; an annular outer piece and a central core. Thus, the pole piece 11 is secured to the pole piece support 13 through the pole stem comprised of the annular body 41 and the cylindrical core 42. An annular air gap 48 is defined between the elements 41 and 42 of the pole stem, and the air gap 48 extends from the pole piece support 13 to the pole piece 11. The pole piece 12 is similarly secured to the pole piece support 14 through the intermediary of a pole stem comprised of annular element 43 and cylindrical core 44 having an annular air gap 49 between them.

Magnetic flux developed by the coil 20 flows through the pole stem elements 41 and 42 and into the pole piece 11. The magnetic flux leaves the pole piece 11 and crosses the gap 15 to enter the pole piece 12. The flux then travels through the pole stem comprised of pieces 43 and 44 into the pole piece support 14 and returns through the columns 16-19 and the pole piece support 13. The magnetic flux developed by the coil 21 follows the same path as the flux developed by the coil 20.

The two-piece construction of the pole stems with the annular air gap between the pole stem elements saves weight while at the same time improving magnetic field uniformity across the face of the pole pieces. Most of the magnetic flux delivered to the pole piece 11, for example, will flow through the pole stem parts 41 and 42 with a negligible amount of flux flowing through the air gap 48. Flux delivered to the pole piece 11 through the pole stem parts 41 and 42 distributes itself within the pole piece 11 so as to be sufficiently uniform to carry out the magnetic resonance studies intended. Additionally, shim bars comprised of annular ferromagnetic members 22, 23 are each disposed on a face of a respective one of the pole pieces 11, 12. The shim bars 22, 23 are approximately the pole diameter and typically have a beveled inner surface facing the pole piece center. The shim bars improve the uniformity within the gap 15.

Conventional magnetic resonance magnets having column supports utilize a uniform column, typically circular cylindrical. Important features of the present invention reside in the columns 16-19 which are shaped to achieve the various results described below.

The column 18 has an upper base portion 51 and a lower base portion 52 which are the widest parts of the column 18. The upper pole piece support 13 rests on the base portion 51, and the base portion 52 rests on the lower pole piece support 14. The middle portion 53 of the column 18 is the narrowest part of the column, and it is also the part of the column having the greatest dimension in the radial direction relative to the pole pieces. The transition portion 54 of the column 18 extends between the base portion 51 and the middle portion 53. The radial dimension of the transition portion 54 progressively increases the further the distance from the base portion 51 and toward the middle portion 53. The width of the transition portion 54 similarly decreases from the maximum column width at the base portion 51 to the minimum column width of the middle portion 53 the further the distance from the base portion 51 and toward the middle portion 53. The transition portion 55 similarly spans between the base portion 52 of the column and the middle portion 53. The dimensions of the columns in the radial direction are seen in FIG. 2 for columns 16 and 18, and the width dimensions of the columns are seen for column 17.

The magnet structure is symmetrical about an imaginary plane midway between the pole pieces 11 and 12. Consequently, as discussed in connection with FIG. 1, the columns 16–19 require a cross section at the midplane which is the minimum cross section required for the columns in order to avoid magnetic saturation. The middle portion 53 of the column 17 has that minimum cross section which extends over a certain distance on opposite sides of the magnet midplane. At a position approximately opposite the magnet shim bar 22, the transition portion 54 begins to flare outwardly to the width of the base portion 51. The cross-sectional area of the transition portion 54 progressively increases along the direction toward the base portion 51. Finally, at the base portion 51 the column 18 exhibits its maximum cross-sectional area.

Figure 5:
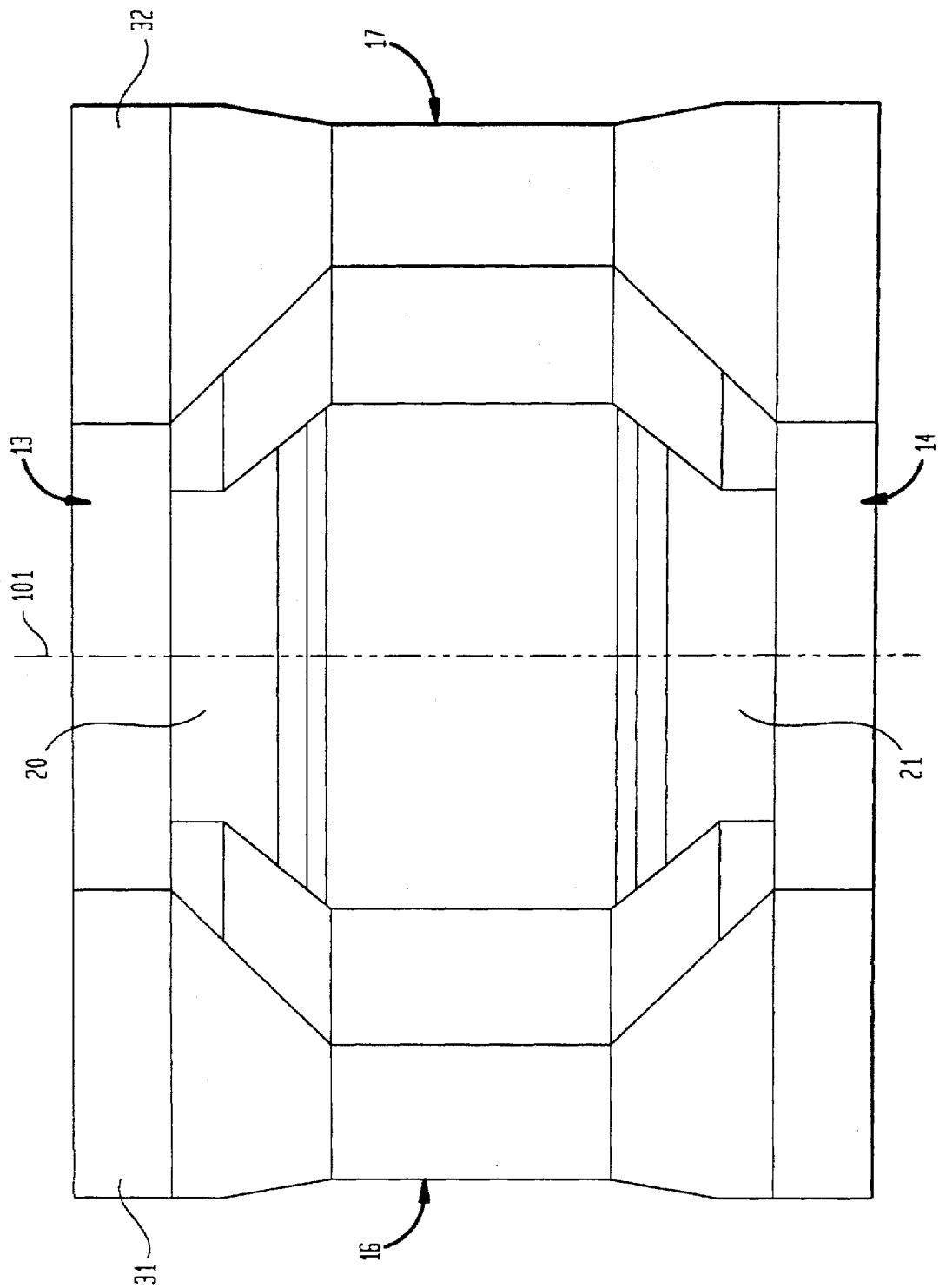
FIG. 5 is an elevation of the magnet according to the invention viewed from the direction V in FIG. 3.

The magnet would exhibit the best possible field uniformity if it were a body of revolution, e.g. if a continuous peripheral wall supported the upper pole piece support 13, instead of separate columns spaced from each other. On the other hand, from a clinical standpoint it is desirable to maximize access to the patient-receiving gap 15. Maximum access is desirable to facilitate the placement and positioning of large patients, and patients that require life support equipment, as well as to reduce claustrophobic reactions. As a consequence, the middle portion 53 of column 18, and of all the columns, is made narrow in order to expand the distance between adjacent columns at their respective middle portions, and to provide ample access to the patient-receiving gap 15. The degree of access provided by this feature is shown in FIG. 5 which is a vertical elevation of the magnet taken along the line of sight indicated by the arrow V in FIG. 3. The narrowing of the columns at their middle portions which extend approximately the full height of the gap 15 provides a large opening for access to the patient-receiving gap.

In order to provide a sufficiently large cross sectional area at the narrowed column middle portion, the column middle portion has the greatest radial dimension. This radial dimension decreases through the transition portions to the base portions of the column. The widening of the transition portions and the base portions of the columns occurs where the magnetic leakage field is strongest and improves the symmetry of the magnet structure which interacts with the stronger leakage field. This improves field uniformity within the gap. Consequently, the columns of the magnet having the structure according to the present invention constitute shimming structure for shimming the magnetic field of the magnet.

Figure 6:
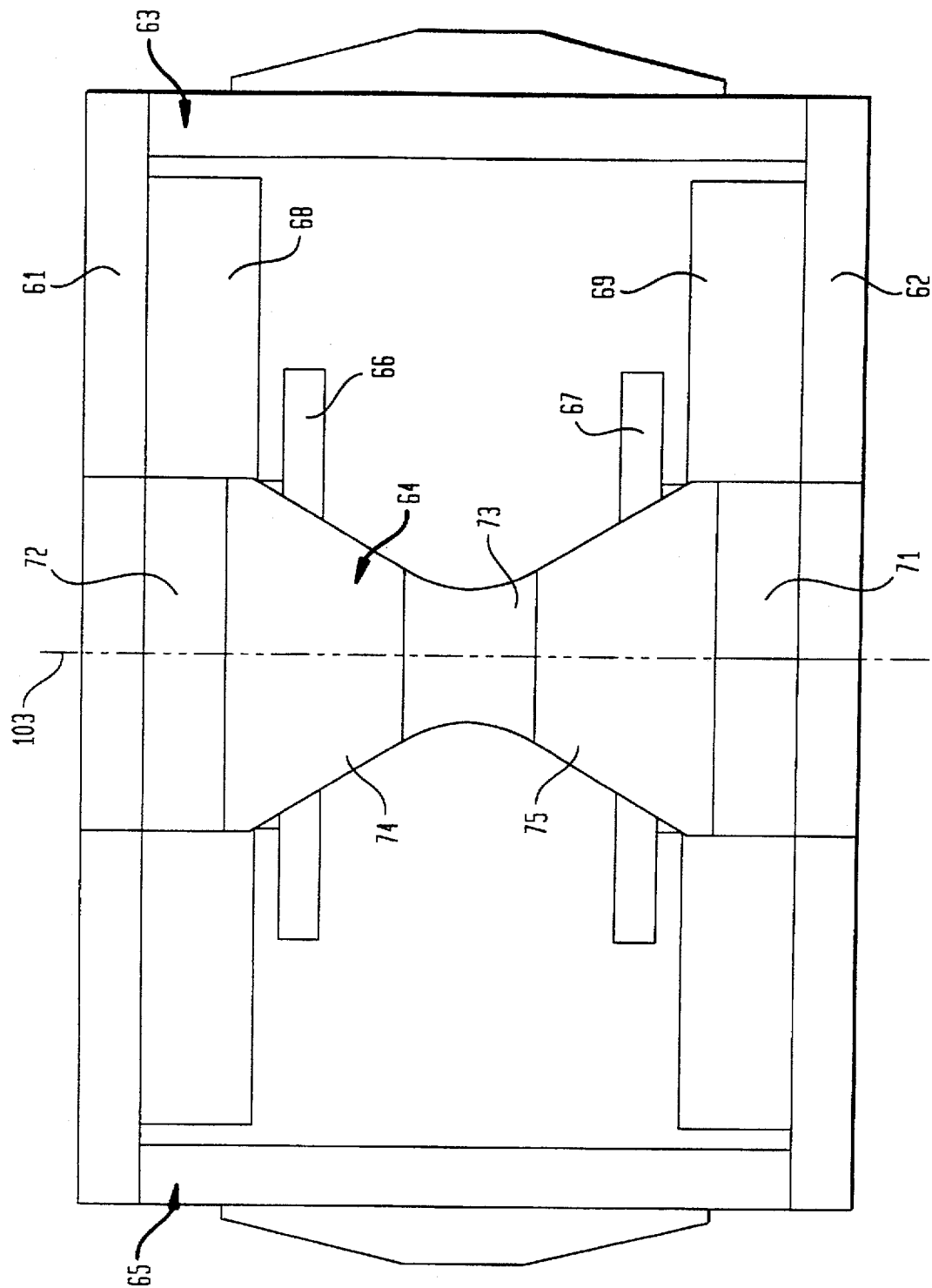
FIG. 6 is a front elevation of another embodiment of the magnet according to the invention.

Another embodiment of the invention, also having four columns, is shown in FIG. 6. This magnet is similar to the previously described embodiment in that it is comprised of upper and lower pole piece supports 61 and 62. The upper pole piece support 61 is held in position by columns 63–65 and a fourth which is not shown. The magnet central axis is shown at 103. Pole piece and shim bar combinations 66, 67 are supported by pole stems (not shown). Electromagnet coils 68, 69, each surrounding a respective pole stem in the manner previously described, develop the magnetic field.

The columns 63–65 are shaped to closely meet the criteria of constant magnetic field in every cross section along the length of the columns. For example, column 64 has a pair of base portions 71, 72 at its opposite ends which engage the respective pole piece supports 61, 62. Middle portion 73 is the most narrow part of the column 64, but it is also the thickest part of the column. A transition portion 74 extends between the middle portion 73 and the base portion 72, and another transition portion 75 extends between the middle portion 73 and the base portion 71. In the transition portions 74 and 75 the thickness or radial dimension of the column 64 tapers from its maximum thickness at the middle portion 73 down to its minimum thickness at the base portions 71 and 72.

In this embodiment the middle portion does not maintain a constant width over an appreciable part of the distance between the pole pieces. Rather, the middle portion 73 is narrowest at the midplane of the magnet and then progressively widens at positions progressively closer to the base portions of the column. This allows the cross sectional area of the column to be no larger than just that required to achieve a constant magnetic field within the column and thus helps achieve material and weight minimization.

The previously disclosed embodiments of the magnets according to the invention have circular pole pieces. The invention is not limited in this regard.

Figure 7:
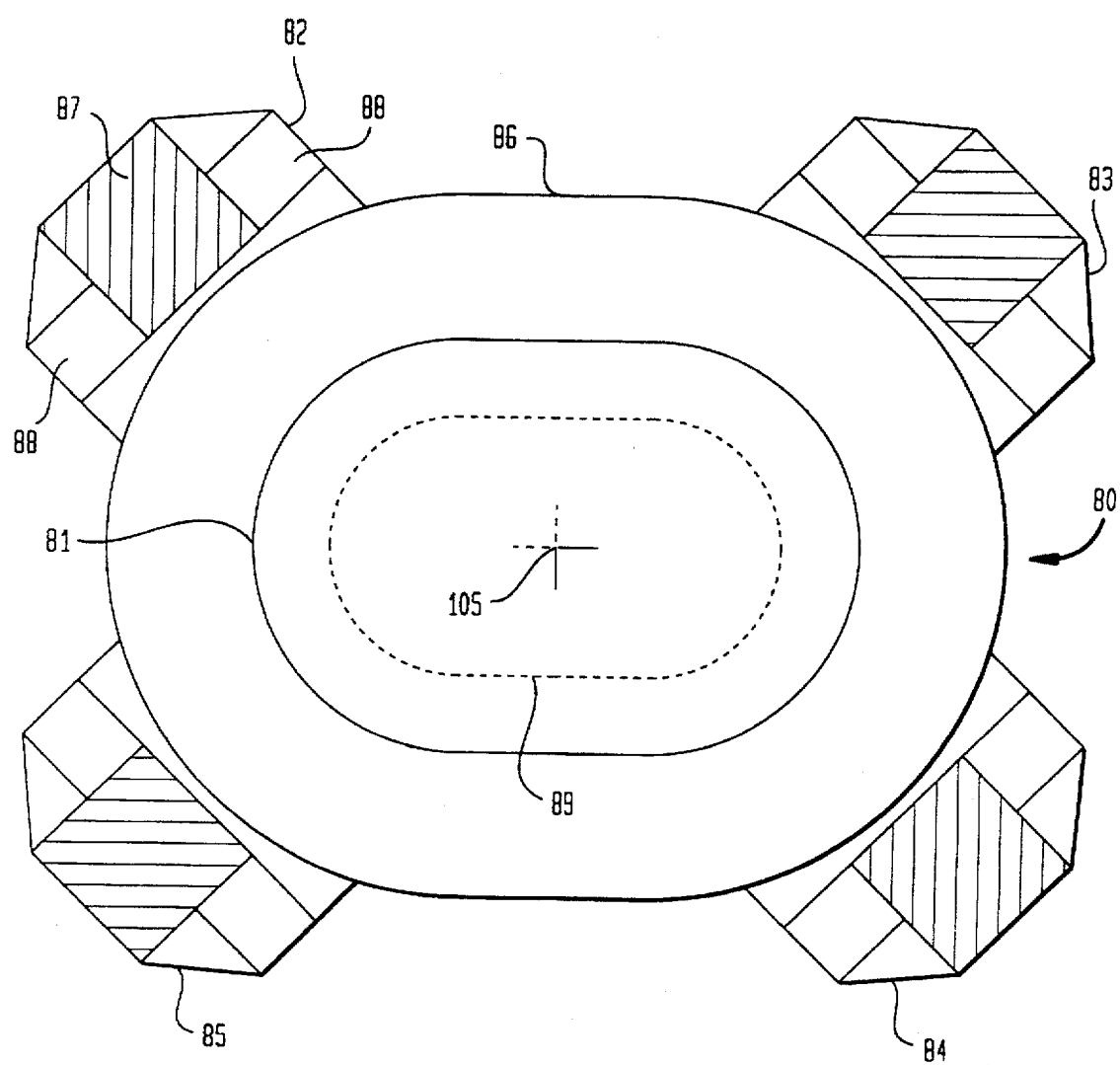
FIG. 7 is a horizontal section of through the horizontal midplane a third embodiment of the magnet according to the invention having oval pole pieces.

FIG. 7 is a plan view of a cross section taken along the horizontal midplane of a magnet according to the invention having oval poles. The magnet central axis is shown at 105. A pole piece support 80 has mounted thereon an oval pole 81. Four vertical columns 82–85, shown in cross section, extend to and support a second pole piece support (not shown) which is identical to the pole piece support 80. Each vertical column 82–85 has a cross section like those previously described. Thus, column 82 has a cross section with a narrow middle portion 87 extending radially outwardly from the pole piece, and a base portion 88 which extends generally circumferentially relative to the pole. The other columns 83–85 have the same shape. The magnetic field is developed by the electromagnet coil 86. The coil 86, and the pole stems (not shown) are oval and generally congruent with the oval pole 81. Alternatively, where the degree of ovality of the poles is not large, the coil and pole stems may be circular.

The oval pole 81 develops a magnetic field which is sufficiently uniform within a region of space 89 to carry out the intended magnetic resonance study. This could include imaging, spectroscopy, relaxation time numerical measurements or some other study. The study region 89 is also oval as a consequence of the pole piece shape. More particularly, the pole 81 has a major dimension which extends in the direction between the pair of columns 82 and 83, and also 84 and 85. Accordingly, the study region 89 will be elongated and have its major dimension extending between the pair of columns 82 and 83 (and also 84 and 85).

The elongated study region 89 allows preferential orientation of a patient depending upon the part of the patient's anatomy which is to be studied. For example, if abdominal images are going to be made, the patient will preferably be inserted lengthwise between columns 82 and 85 (or 83 and 84) so that the patient's spine lies along the major dimension of the study region 89.

The illustrated embodiment has columns 82–85 laid out in a rectangular pattern. Depending upon the degree of ovality of the magnet poles, the columns can be positioned on a rectangular pattern or a square pattern.

Different column shapes which approximate the criteria of constant magnetic field strength within the columns along their length can be adopted. Additionally, a permanent magnet, or a superconducting electromagnet, can be used in place of the disclosed resistive electromagnet. Accordingly, the particular disclosed embodiments should be taken as exemplary and not limiting, and the scope of patent rights are defined by the following claims.

I claim:

1. A magnet, for use in medical magnetic resonance studies, comprising:

a pair of opposed ferromagnetic pole pieces disposed facing each other said pole pieces defining therebetween a patient-receiving gap for receiving a patient to be examined by magnetic resonance and a magnet central axis extending between said pole pieces through said gap, whereby radial and circumferential dimensions are defined with respect to said magnet central axis;

a ferromagnetic yoke comprising means for mounting said pair of ferromagnetic pole pieces in their respective positions facing each other, said ferromagnetic yoke comprising a lower support for supporting one of said pole pieces in a lower position, an upper support for supporting the other of said pole pieces in an upper position above said lower pole piece, and four ferromagnetic columns extending between said upper support and said lower support, and said upper and lower supports jointly comprising a magnetic flux return path for magnetic flux crossing said gap from one to the other of said pole pieces;

said four ferromagnetic columns approximately equispaced circumferentially around said magnet central axis and defining spaces between them, a pair of adjacent columns having cross sections effective to maintain an approximately constant magnetic field along the length of said columns, and said pair of adjacent columns each having a respective cross section having a maximum radial dimension and a minimum circumferential dimension midway between said upper and lower supports and said respective column cross sections becoming progressively shorter in the radial dimension and progressively longer in the circumferential dimension along the length of said columns toward said supports for maximizing the distance between said pair of adjacent columns midway between said supports to facilitate insertion and removal of a patient in the magnet gap; and means for generating a magnetic field between said pair of poles.

2. A magnet according to claim 1, further comprising means for shimming the magnetic field within the gap between said pair of pole pieces to a uniformity sufficient to allow a medical magnetic resonance study to be performed on a patient while within the gap.

3. A magnet, for use in medical magnetic resonance studies, comprising:

a pair of opposed ferromagnetic pole pieces disposed facing each other said pole pieces defining therebetween a patient-receiving gap for receiving a patient to be studied by magnetic resonance and a magnet central axis extending between said pole pieces through said gap, whereby radial and circumferential dimensions are defined with respect to said magnet central axis;

a ferromagnetic yoke comprised of ferromagnetic upper and lower pole supports each for supporting a respective one of said ferromagnetic pole pieces facing each other, and a plurality of ferromagnetic columns for supporting said upper pole support above said lower pole support, said upper and lower pole supports and said columns jointly establishing a magnetic flux return path for magnetic flux which passes from one pole piece to the other through said air gap, and said yoke and pole pieces being symmetrical about an imaginary plane passing midway between said pole pieces and parallel thereto;

each of said columns having a respective cross section which is minimum in the region midway between said pole supports and which increases in directions toward each of said pole supports;

said columns each having a respective cross section having a maximum radial dimension and a minimum circumferential dimension midway between said upper and lower pole pieces and said respective column cross sections becoming progressively shorter in the radial dimension and progressively longer in the circumferential dimension along the length of said columns toward said supports and terminating at said supports with a maximum circumferential dimension, and means for generating magnetic flux flowing from one to the other of said pole pieces across said pole pieces; and shimming means for shimming the magnetic field within the air gap between said pair of pole pieces to a uniformity sufficient to allow a medical magnetic resonance study to be performed on a patient while within the air gap.

4. A magnet according to claim 3, wherein the respective cross sectional area of each of said columns increases in directions toward said pole supports such that the magnetic field through every cross section is approximately constant.

5. A magnet according to claim 3, wherein said columns are disposed uniformly around said axis.

6. A magnet according to claim 3, wherein the distance between adjacent columns is sufficient to allow the insertion of a patient between adjacent columns into said gap.

7. A magnet according to claim 3, wherein said pair of pole pieces are circular.

8. A magnet according to claim 3, wherein said pair of pole pieces and said means for shimming are effective to develop a uniform region of magnetic field sufficiently large to simultaneously carry out magnetic resonance scanning on two human patients.

9. A magnet according to claim 3, wherein said plurality of columns are comprised of four columns disposed at relative distances so as to be positioned on the corners of a rectangle;

the respective distances between adjacent columns is sufficient to allow the insertion of a patient between adjacent columns into said gap.

10. A magnet according to claim 9, wherein said pair of pole pieces are circular.

11. A magnet according to claim 9, wherein said pair of pole pieces are oval having a major transverse dimension and a minor transverse dimension, and said pair of pole pieces are oriented with their major transverse dimensions aligned with the length dimension of the rectangle on which said columns are situated.

12. A magnet according to claim 3, wherein said means for shimming further includes terminating regions of maximum circumferential dimension of said columns.

13. A magnet according to claim 3, wherein
said means for shimming further comprises a pair of ferromagnetic rings each disposed on a respective pole face about the periphery thereof.

14. A magnet according to claim 3, wherein
said pole supports are each comprised of a ferromagnetic plate-like member having a central region to which a respective one of said pole pieces is attached and a peripheral region at which said columns are attached.

15. A magnet according to claim 14, wherein
said plate-like members comprising said supports having a peripheral region comprised of a plurality of legs extending outwardly from said central region and equal in number to the number of said columns, and each of said columns connected to a respective one of said legs.

16. A magnet according to claim 3, wherein
said means for generating magnetic flux is a resistive electromagnet.

17. A magnet according to claim 3, wherein
said yoke further comprises a pair of ferromagnetic pole stems, each of said pole stems extending from the central region of a respective one of said supports toward the other of said supports, and each of said pole stems having a respective one of said pole pieces mounted thereon; and said means for generating magnetic flux is comprised of an electromagnet winding.

18. A magnet according to claim 3, wherein
said means for generating magnetic flux is a superconducting electromagnet.

19. A magnet according to claim 3, wherein
said yoke, pole pieces and means for generating magnetic flux is effective to generate a magnetic field of at least 5000 gauss within said gap.

\* \* \* \* \*